US00PP24513P3

(12) United States Plant Patent

Olesen et al.

(10) Patent No.: US PP24,513 P3

(45) Date of Patent: Jun. 3, 2014

(54) *CLEMATIS* PLANT NAMED 'EVIPO055'

(50) Latin Name: *Clematis viticella*
Varietal Denomination: Evipo055

(75) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 12 days.

(21) Appl. No.: 13/507,014

(22) Filed: May 31, 2012

(65) Prior Publication Data

US 2013/0326775 P1 Dec. 5, 2013

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Kent L Bell

(57) ABSTRACT

A new *Clematis* plant with a compact growth habit, profuse, white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo055'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1994 and the resulting seeds were planted the following winter in a controlled environment in Guernsey, Channel Islands, United Kingdom. The new variety named 'Evipo055' originated as a single seedling from the stated cross.

The new *clematis* plant may be distinguished from its female seed parent and male pollen parent primarily by flower color and growth habit.

The objective of the hybridization of this *clematis* plant was to create a new and distinct variety for nursery culture with unique qualities such as:

1. Uniform and abundant white flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo055' was selected by Mogens N. Olesen and Raymond J. Evison in their *clematis* development program in the Channel Islands, United Kingdom in 1995. Asexual reproduction of 'Evipo055' by means of vegetative cuttings and traditional layering was first performed by Mogens N. Olesen and Raymond J. Evison in the nursery during the summer of 1995. This initial and subsequent asexual propagations have demonstrated that the characteristics of 'Evipo055' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo055'.

Specifically illustrated in FIG. 1. are flowers at various stages of development, flower in parts, FIG. 2. leaves, and stems.

DETAILED DESCRIPTION OF THE VARIETY

Figure 1:
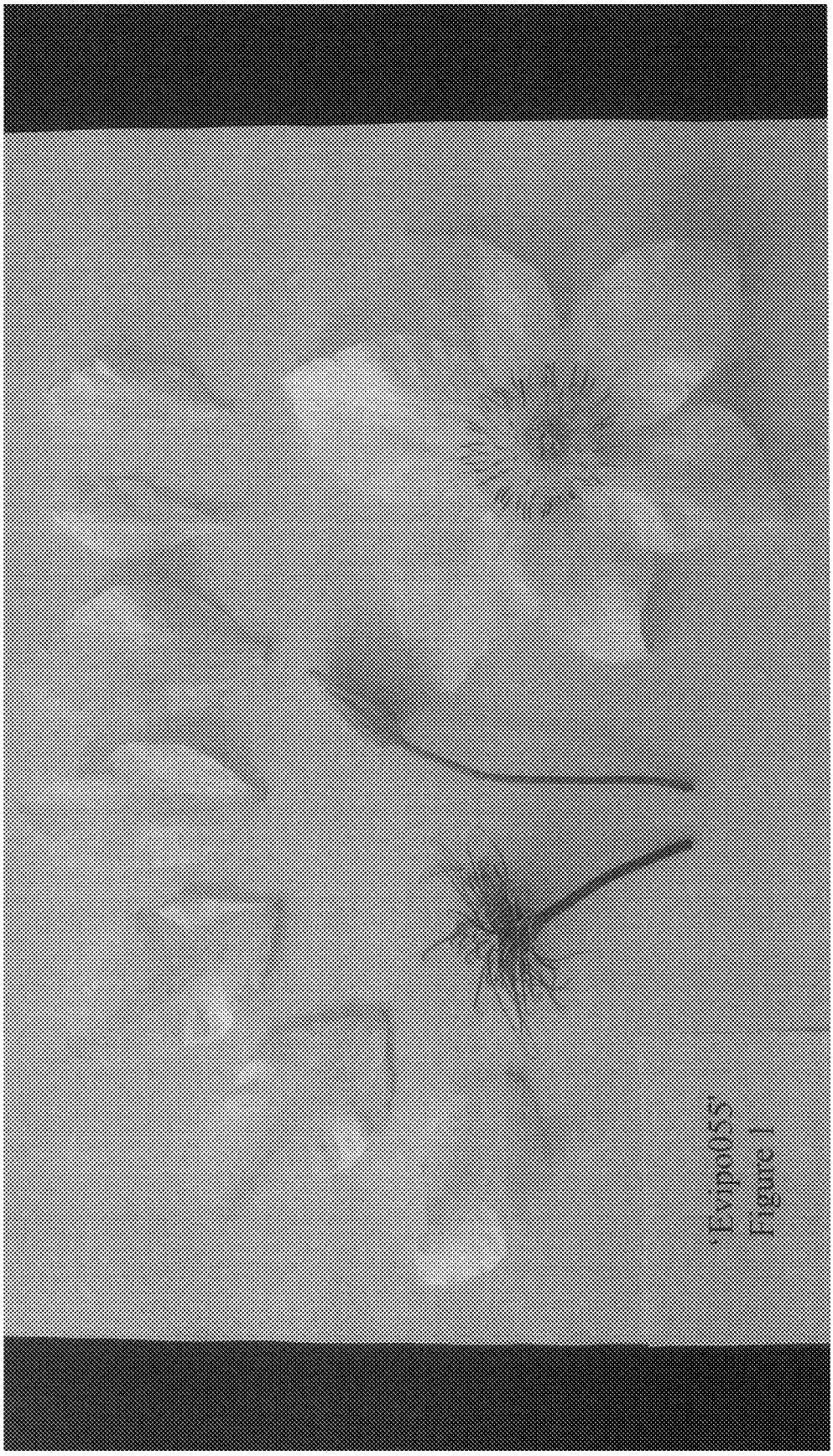
Figure 2:
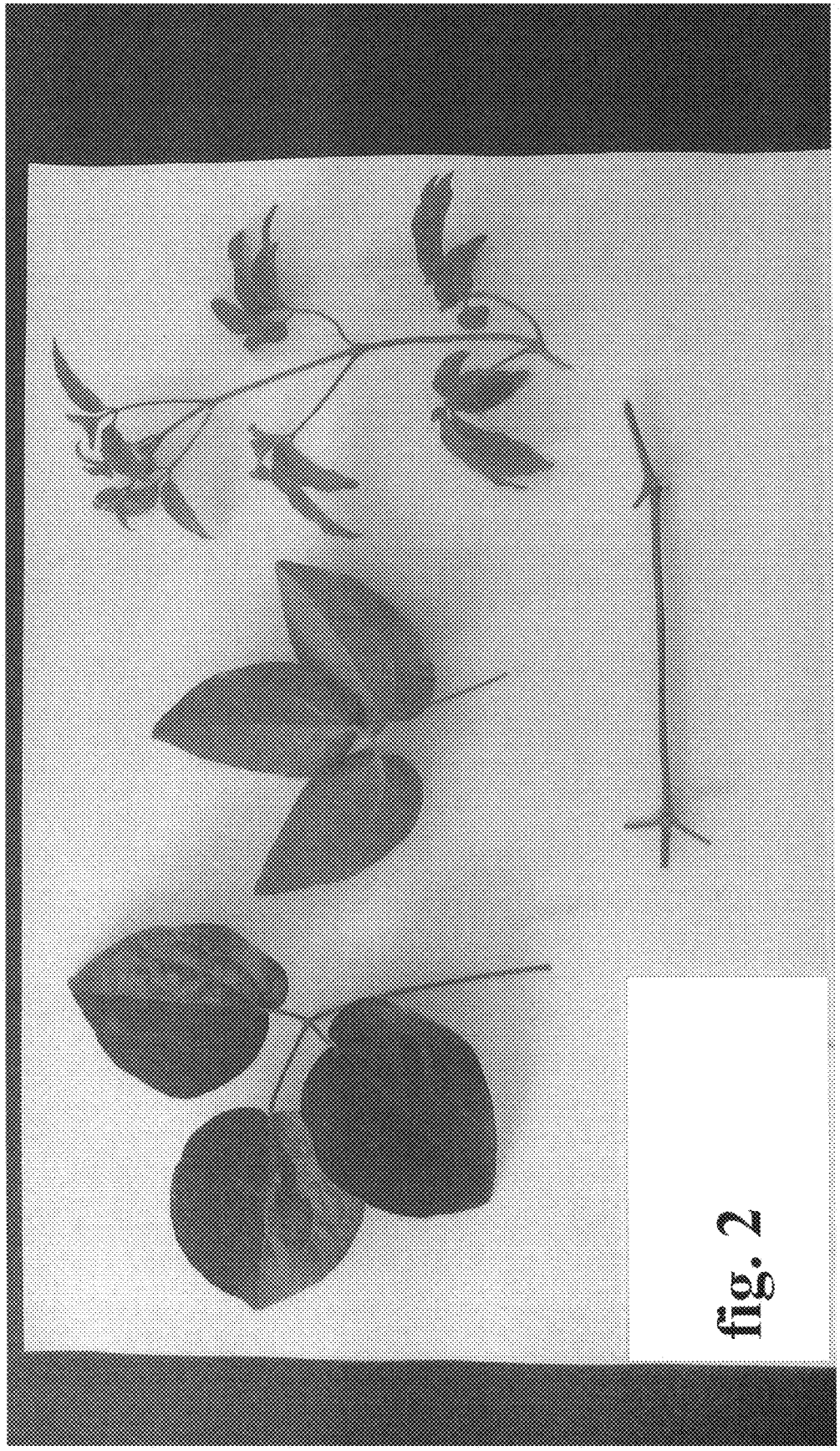

The following is a detailed description of 'Evipo055', as observed in its growth throughout the flowering period in glasshouses the Netherlands. Observed plants were cultivated for a period of 18 months in 17 cm containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evitwo' described and illustrated in U.S. Plant Pat. No. 10,167 are compared to 'Evipo055' in Chart 1.

CHART 1

| | 'Evipo055' | 'Evitwo' |
|---|---|---|
| Flower diameter | 135 mm. | 100 to 180 mm |
| General tonality of flower color | White Group 155D | White Group 155C |
| Tepal count | 6 | 12 |

FLOWER AND FLOWER BUD

Blooming habit: Continuous. The natural flowering period is generally from April to September. Flowers on new and old growth.

Flower bud:

*Size*.—Length 28 mm, diameter 14 mm.

*Tepal color*.—At ¼ opening, White Group 155B.

Bud form: Elliptic.

Pedicel:

*Length*.—75 mm.

*Diameter*.—About 1 mm.

*Texture*.—Smooth.

*Strength*.—Moderate.

Receptacle: Not present. Tepals attach directly to pedicel.

Flower arrangement:

*Borne*.—Singly.

Flower bloom:

*Size*.—Diameter 135 mm. 10 mm deep.

*Shape from the side*.—Flat.

*Fragrance*.—None.

*Lasting quality*.—Flowers normally remain 10 days on the plant.

*General tonality*.—White Group 155D.

Tepals:

*Upon opening*.—Upper surface is White Group 155D. Lower surface is White Group 155C.

*After opening*.—Upper surface is White Group 155D. Lower surface is White Group 155C.

*Quantity*.—Normally 6 tepals.

*Size*.—65 mm in length by 37 mm wide.

Shape: Individual tepal shape is elliptic. The tepal apex is acuminate. The tepal base is typically acute.

*Apex recurvature*.—Flat.

*Margins*.—Entire. Weak undulations of margin observed.

*Persistence*.—Tepals drop off cleanly.

Reproductive organs:

*Arrangement*.—Open.

*Pollen*.—None observed.

*Anthers*.—Size: 6 mm in length. Color: Greyed Yellow Group 161A. Quantity: On average, 65.

*Filaments*.—Color: White Group 155C. Length: 8 mm on average.

*Pistils*.—Quantity: On average, 25.

*Stigmas*.—White Group 155A.

*Styles*.—Color: White Group 155A. Length: On average, 10 mm.

PLANT

Size: Seasons growth attains 1.8 meters in height. About 45 cm wide.

Stems:

*Color*.—Juvenile stems are Yellow-Green Group 145B. Mature stems are Greyed-Orange Group 166B.

*Internodes*.—On average, 7 cm between nodes.

*Length*.—Normally 50 to 80 cm from the base of the plant to the flowering portion of the stem.

*Diameter*.—About 3 mm.

*Texture*.—Mature stems are ribbed. Juvenile stems are smooth.

Plant foliage:

*Arrangement*.—Ternate.

*Leaf characteristics*.—Deciduous.

*Leaf size*.—Compound leaves are 80 mm (l)×120 mm (w). Leaflets are normally 55 mm (l)×45 mm (w).

*Abundance*.—On average 2 leaves per 10 cm of stem.

*Petioles*.—Size: Normally 10 mm in length by 1.5 mm diameter. Texture: Smooth. Color: Yellow-Green Group 144A.

*Petioloule*.—Size: Normally 20 to 25 mm in length by 1.5 mm diameter. Texture: Smooth. Color: Yellow-Green Group 144A.

Leaf color: Juvenile upper Yellow-Green Group 144A. Juvenile lower Yellow-Green Group 144A. Mature upper Yellow-Green Group 146A. Mature lower Yellow-Green Group 146B.

Leaflet shape: Generally cordate. The base is cordate to rounded, the apex is acute to widely acute.

*Margin*.—Entire.

*Surface*.—The upper side is smooth. The lower side is smooth.

*Thickness*.—Moderate.

*Glossiness*.—Moderately Glossy.

Disease resistance: Subject to any disease that normally attacks the species. However the variety is more tolerant to *clematis* wilt than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo055', substantially as described and illustrated herein, due to its abundant white flowers with good keepability, attractive foliage and compact growth, year round flowering under glasshouse conditions, suitability for production from softwood cuttings in pots, durable flowers and foliage which make the variety suitable for distribution in the floral industry.

* * * * *